United States Patent [19]

Chu

[11] Patent Number: 4,607,032

[45] Date of Patent: Aug. 19, 1986

[54] QUINO-BENOXAZINE ANTIBACTERIAL COMPOUNDS

[75] Inventor: Daniel T. Chu, Vernon Hills, Ill.

[73] Assignee: Abbott Laboratories, North Chicago, Ill.

[21] Appl. No.: 604,347

[22] Filed: Apr. 26, 1984

[51] Int. Cl.⁴ .................. A61K 31/535; C07D 498/06
[52] U.S. Cl. ...................., 514/212; 540/575; 514/211; 514/218; 514/222; 514/232; 514/233; 514/236; 544/58.6; 544/73; 544/99
[58] Field of Search ............ 544/73, 99, 58.6; 260/243.3; 424/246, 248.52, 248.53, 248.55; 514/211, 212, 218, 222, 232, 233, 236

[56] References Cited

U.S. PATENT DOCUMENTS

| | | | |
|---|---|---|---|
| 4,017,622 | 4/1977 | Minami et al. | 424/250 |
| 4,292,317 | 9/1981 | Pesson | 424/250 |
| 4,382,892 | 5/1983 | Hayakawa et al. | 544/101 X |
| 4,439,436 | 3/1984 | Wentland et al. | 424/258 |
| 4,443,447 | 4/1984 | Gerster et al. | 544/101 X |
| 4,473,568 | 9/1984 | Hutt | 544/101 X |

FOREIGN PATENT DOCUMENTS 78362   5/1983   European Pat. Off. .
1147336 4/1969   United Kingdom .

OTHER PUBLICATIONS

DAUC, 84-039639/07, J59001,489-A (1984).
DAUC, 84-043150/08, EP101,829A (1984).

*Primary Examiner*—Richard L. Raymond
*Attorney, Agent, or Firm*—Martin L. Katz; Steven F. Weinstock; Robert W. Stevenson

[57] ABSTRACT

Quino-benoxazine compounds having the formula:

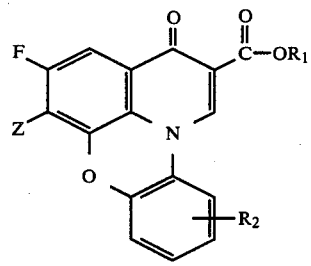

wherein $R_2$ is one or more substituents, $R_1$ is a hydrogen or a carboxy-protecting group and Z is an amine group or an aliphatic heterocyclic group. The compounds have antibacterial activity.

17 Claims, No Drawings

QUINO-BENOXAZINE ANTIBACTERIAL COMPOUNDS

This invention relates to a new quino-benoxazine derivatives having antibacterial properties, compositions containing the new quino-benoxazine derivatives and methods of treating mammalian patients with the new quino-benoxazine derivatives.

It is known that certain quinoline compounds exhibit antibacterial properties, notably certain 7-piperazinyl-4-oxo-1,4-dihydroquinoline-3-carboxylic acid derivatives which are substituted in the 1 position with an alkyl, benzyl or acetyl substituent. U.S. Pat. No. 4,292,317 discloses derivatives of 7-piperazinyl-4-oxo-1,4-dihydroquinoline-3-carboxylic acids wherein the 1 position is substituted by an alkyl group or a vinyl group. In U.S. Pat. No. 4,284,629 there are disclosed various 4-oxo-1,4-dihydroquinoline-3-carboxylic acids in which the 1 position is substituted with a cycloalkyl group.

This invention relates to novel antibacterial agents and, more particularly, to 1-substituted amino-2-fluoro-4-oxo-4-H-quino[2,3,4-i,j][1,4]benoxazine-5-carboxylic acid and derivatives thereof having the formula:

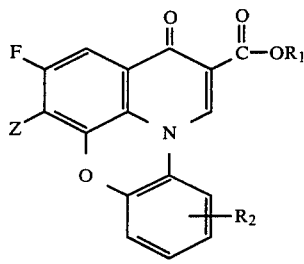

(I)

wherein $R_2$ is one or more of hydrogen, halogen, $C_1$ to $C_6$ alkyl including substituted derivatives thereof, nitro, carboxyl, cyano, methylenedioxy, a group having the formula —Y—$R_3$ wherein —Y— is —O— or —S— and $R_3$ is hydrogen or $C_1$ to $C_6$ alkyl and an amine having the formula:

wherein $R_4$ and $R_5$ are each independently hydrogen or $C_1$ to $C_6$ alkyl.

$R_1$ is hydrogen or a carboxy-protecting group.

Z is an amino group having the formula:

wherein $R_6$ is hydrogen or $C_1$ to $C_{10}$ alkyl as well as the corresponding substituted derivatives thereof; and $R_7$ is alkyl or substituted alkyl, as described above with reference to $R_6$, or an amino group, a mono-($C_1$ to $C_6$) alkylamino group or a di-($C_1$ to $C_6$)alkylamino group.

Alternatively, Z can be an aliphatic heterocyclic ring containing 4 to 7 atoms, and preferably 5 to 6 atoms as well as substituted derivatives thereof.

As used herein, the term "halogen" refers to chloro, bromo, fluoro and iodo groups, while the term "$C_1$ to $C_6$ alkyl" refers to loweralkyl groups including methyl, ethyl, propyl, isopropyl and butyl.

As indicated above, $R_2$ can be $C_1$ to $C_6$ alkyl as well as hydroxy and halo-substituted derivatives thereof. Such groups include a chloromethyl group, a chloroethyl group, a chloropropyl group, a hydroxyethyl group, and a trifluoromethyl group.

$R_2$ can also be a group of the formula —Y—$R_3$. Representative groups of this type include a hydroxy group, a mercapto group, a lower alkoxy group, such as methoxy, ethoxy, propoxy, as well as the thio analogs thereof, namely a methylmercapto group, and an ethylmercapto group.

As used herein, the term "carboxy-protecting group" refers to and includes the residue of a carboxylic acid ester group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. In general, such carboxy-protecting groups can be relatively easily cleaved to yield the corresponding free carboxy group. Representative protecting groups include $C_1$—$C_8$ alkyl (e.g., methyl, ethyl, tertiary butyl), substituted alkyl (e.g., dimethylaminoethyl), benzyl and substituted derivatives thereof such as alkoxy and nitrobenzyl groups; also suitable are acyl groups such as pivaloyloxymethyl groups.

The aliphatic heterocyclic rings representing Z are, in accordance with the preferred practice of the invention, aliphatic heterocyclic rings containing 1 or 2 hetero atoms which are selected from the group consisting of S, O and N, with the remaining atoms in the aliphatic heterocyclic ring being carbon atoms, as well as substituted derivatives thereof. In accordance with the practice of the invention, the aliphatic heterocyclic ring has the formula:

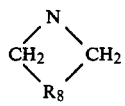

wherein $R_8$ is selected from the group consisting of dimethylene and a group of the formula —$CH_2$—$R_9$—$CH_2$ wherein $R_9$ is selected from the group consisting of —S—, —O—, —N— and —$CH_2$—. Also included are substituted derivatives of such heterocyclic rings wherein the substituent is one or more of a $C_1$ to $C_6$ alkyl group, $C_1$ to $C_6$ hydroxyalkyl, hydroxy, alkanoyl containing 1 to 6 carbon atoms, alkanoylamido containing 1 to 6 carbon atoms and an amino group having the formula:

wherein $R_{10}$ and $R_{11}$ are each independently selected from the group consisting of hydrogen, $C_1$ to $C_6$ alkyl, halo-substituted $C_1$ to $C_6$ alkyl and hydroxy-substituted $C_1$ to $C_6$ alkyl.

Illustrative of such heterocyclic groups are azetidinyl groups, piperazinyl groups, 4-acylpiperazinyl groups, piperidinyl groups, pyrrolidinyl groups, morpholino groups, thiomorpholino groups and homopiperazinyl groups (i.e., hexahydro-1-H-1,4-diazepinyl).

The preferred compounds of the present invention are those having the formula:

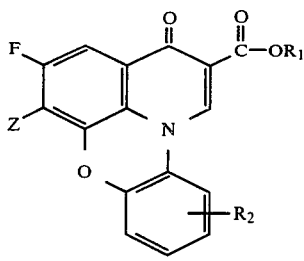

wherein Z is piperazinyl or substituted piperazinyl or 1-(3-amino or substituted amino)pyrrolidinyl as described above, $R_1$ is as described above and is preferably hydrogen, and $R_2$ is hydrogen or one or more of alkyl, halogen, hydroxy or methylenedioxy.

Representative of such preferred compounds are 1-(1-piperazinyl)-2-fluoro-4-oxo-4H-quino[2,3,4-i,j][1,4]benoxazine-5-carboxylic acid, 1-[1(4-methyl)-piperazinyl]-2-fluoro-4-oxo-4H-quino[2,3,4-i,j][1,4]benoxazine-5-carboxylic acid, 1-(3-aminopyrrolidinyl)-2-fluoro-4-oxo-4H-quino[2,3,4-i,j][1,4]benzoxazine-5-carboxylic acid, 1-(1-piperazinyl)-2,10-fluoro-4-oxo-4H-quino[2,3,4-i,j][1,4]benzoxazine-5-carboxylic acid, 1-[1-(4-methyl)piperazinyl]-2-fluoro-4-oxo-4H-quino[2,3,4-i,j][1,4]benzoxazine-5-carboxylic acid, 1-(3-aminopyrrolidinyl)-2-fluoro-4-oxo-4H-quino[2,3,4-i,j][1,4]benzoxazine-5-carboxylic acid.

Also included within the scope of the present invention are pharmaceutically acceptable salts of the foregoing compounds. As used herein, the term "pharmaceutically acceptable salts" refers to nontoxic acid addition salts and alkaline earth metal salts of the compounds of Formula I. The salts can be prepared in situ during the final isolation and purification of the compounds of formula I, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts. It has been found that the compounds of the present invention possess antibacterial activity against a wide spectrum of gram positive and gram negative bacteria, as well as enterobacteria. The compounds of the invention are therefore useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebsiella, Pseudomonas, Acinetobacter, Proteus, Citrobacter, Nisseria, Baccillus, Bacteroides, Peptococcus, Clostridium, Salmonella, Shigella, Serratia, Haemophilus, Brucella, and other organisms. In addition to exhibiting highly effective antibacterial activity, the compounds of the invention exhibit increased and improved solubility characteristics as compared with prior quinoline-3-carboxylic acid compounds in the art.

The compounds of Formula I may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula I of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four times per day.

Compounds according to this invention can be prepared by the reaction illustrated below:

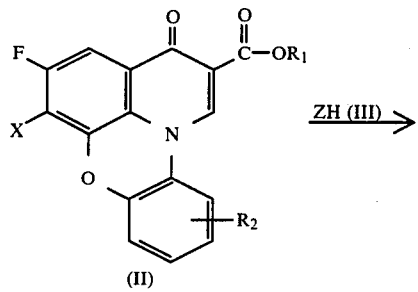

(II)

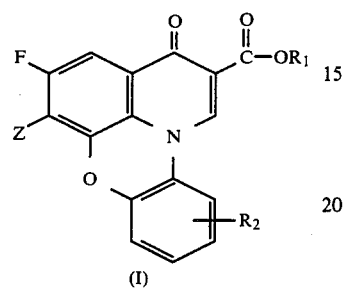

(I)

wherein X is a halogen and R₂ and Z are the same as described above.

The reaction may be performed by heating a compound of the formula (II) with an amine of formula (III) at a temperature of from 20° C. to 200° C., and preferably from 70° C. to 150° C., in the presence of a suitable organic polar solvent such as dimethylsulfoxide, sulfolane, dimethylformamide, dimethylacetamide, 1-methyl-2-pyrrolidinone or water. It is desirable to carry out the reaction in the presence of an acid-acceptor such as triethylamine, potassium carbonate and the like at a molar ratio of 1.0 to 1.2 mole of the acid-acceptor per mole of the compound of the formula (II). The amine (III) can also be used as acid acceptor in which 2 or more molar excess of this reagent is used. The compounds of the formula (II) may be prepared in accordance with the following reaction scheme, in which R₂ is as described above, and X can be independently identical or nonidentical halogen:

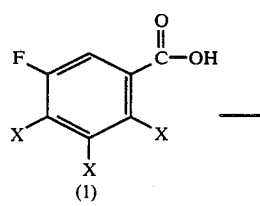

(1)

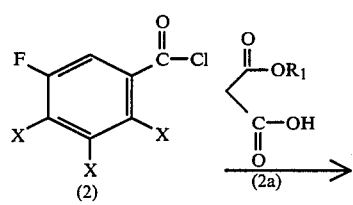

(2)   (2a)

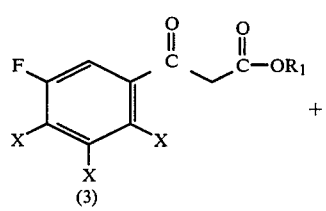

(3)

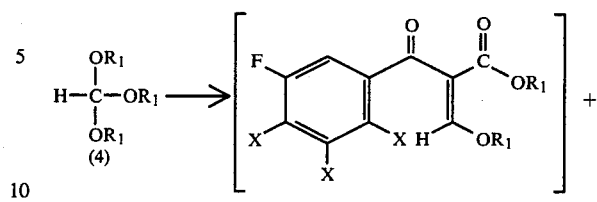

(4)

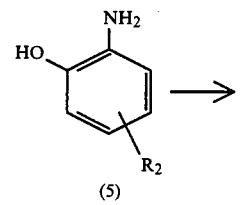

(5)

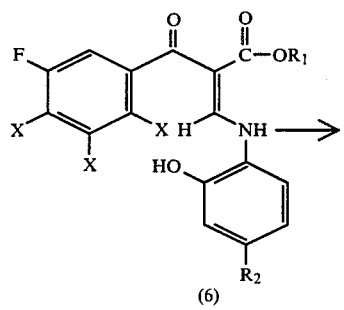

(6)

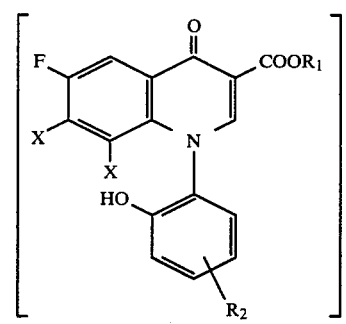

(6a)

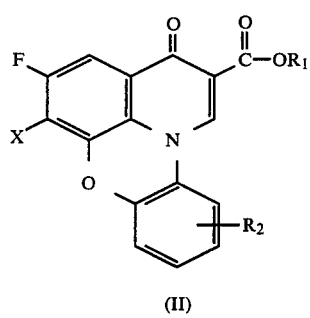

(II)

In accordance with the foregoing reaction scheme, the 2,3,4-trihalo-5-fluorobenzoic acid (1) is treated with thionyl chloride to produce the corresponding acid chloride (2). Displacement of the acid chloride (2) with malonic acid half ester (2a) in the presence of n-butyl lithium yields the β-ketoester (3).

The β-ketoester (3) is then treated with a trialkylorthoformate (4) in the presence of an acid anhydride, preferably acetic anhydride, followed by reaction with substituted or unsubstituted O-hydroxyaniline (5) to obtain the enaminoketoester (6). In the trialkylorthoformate (4), $R_1$ may be an alkyl group of, for example, from 1 to 10 carbon atoms, but is preferably loweralkyl, such as ethyl. Reaction with the trialkylorthoformate is preferably conducted at elevated temperatures, such as from about 50° C. to about 150° C., preferably from about 100° C. to about 140° C., to obtain an oily liquid, which may be isolated or unisolated, as desired (shown in brackets in the reaction scheme). Reaction of the latter with the substituted or unsubstituted O-hydroxyaniline (5) is preferably conducted in an appropriate aprotic or nonaprotic solvent, preferably methylene chloride or tetrahydrofuran, and may be conducted at room or suitable elevated temperature, as desired.

The enaminoketoester (6) is then cyclized, such as by treatment with a strong base as defined above, preferably sodium hydride, to obtain the 1-chloro-2-fluoro-4-oxo-4H-quino[2,3,4-i,j][1,4]benoxazine-5-carboxylic acid ester (II) ($R_1$=alkyl) through the intermediate (6a). Cyclization is conducted in the presence of an aprotic solvent, such as dimethoxyethane, bis(2-methoxyethyl)ether, dimethylformamide, tetrahydrofuran or chlorobenzene, and is preferably conducted at temperatures of about 20° C. to about 145° C., more preferably at the reflux temperature of the solvent employed.

The ester (II) is subjected to hydrolysis, such as by treatment with sodium hydroxide, or dilute mineral acid to form the free acid (II) ($R_1$=H).

The 4-oxo-4H-quino[2,3,4-i,j][1,4]benoxazine-5-carboxylic acid (I) ($R_1$=H) can then be converted into the corresponding ester (I) ($R_1$=H), if desired, by conventional esterification procedures, such as by treating the free acid (I) ($R_1$=H) with the appropriate alcohol in the presence of an acid catalyst, by converting the free acid (I) ($R_1$=H) into the corresponding acid chloride followed by displacement of the chloro radical with the appropriate alcohol, or by treating the sodium salt of the acid (I) ($R_1$=H) with a suitable reactive halide, such as chloromethylpivalate or dimethylaminoethyl chloride in dimethoxyethane to obtain, for example, the pivaloyloxymethyl ester (I) wherein $R_1$ is $-CH_2OCOC(CH_3)_3$ or dimethylaminoethyl ester (I) wherein $R_1$ is $CH_2CH_2N(CH_3)_2$.

The foregoing may be better understood from the following examples, which are presented for purposes of illustration and are not intended to limit the scope of the inventive concepts. As used in the following examples, the references to compounds, such as (1), (2), (3), etc., and to substituents, such as R, $R_1$, $R_2$, etc., refer to the corresponding compounds and substituents in the foregoing reaction scheme and in formulae I and II.

EXAMPLE 1

1-(1-piperazinyl)-2-fluoro-4-oxo-4H-quino[2,3,4-i,j][1,4]benoxazine-5-carboxylic acid (a) To a solution of 3.9 g. of 2,3,4,5-tetrafluorobenzoic acid in 20 ml. of methylene chloride is added 4 ml. of thionyl chloride. After refluxing for 30 minutes, the reaction mixture is evaporated to dryness to give 4.95 g. of the acid chloride.

This is slowly added to a dry ice-cooled solution of 3.5 g. of malonic acid monoethyl ester in 35 ml. of tetrahydrofuran, 37.9 ml. of 1.4M. n-butyl lithium in THF, and the flask is warmed to $-5°$ C. for 5 minutes and then is cooled back to $-70°$ C. To the resulting solution there is added 4.95 g. of the acid chloride in 10 ml. of THF. The cooling bath is removed, and the solution allowed to warm to room temperature after an hour. The solution is then partitioned between 1N HCl and ether. The ether portion is washed with $NaHCO_3$ and dried over $MgSO_4$, and then evaporated to obtain the liquid β-ketoester (3).

(b) A solution of 20 g. of the above β-ketoester (3) in 18.5 ml. of triethylorthoformate and 45 ml. of acetic anhydride is treated at 135° C. for 1½ hours with the removal of the ethyl acetate formed during the reaction. The solution is evaporated under reduced pressure to a mobile oil. The oil is then dissolved in 200 ml. of methylene chloride and 9.5 g. of o-hydroxyaniline is added into the solution. After 1 hour, the solution is evaporated to dryness and crystallized from 200 ml. of hexane and 5 ml. of ether yielding (6), wherein $R_1$=$C_2H_5$, $R_2$=H, X=F).

(c) To a cold solution of 15 g. of the preceding product (6), $R_1$=$C_2H_5$, X=F, $R_2$=H in 150 ml dimethoxyethane (DME) is slowly added 3.33 g. of a 60% sodium hydride-in-oil suspension. The mixture is refluxed for 24 hours and is cooled and diluted with water to a volume of 1.5 liters. The mixture is then filtered and the solid is washed with a 1:1 hexane/ether solution to obtain (II), ($R_1$=$C_2H_5$, X=F, $R_2$=H).

(d) To a suspension of 7 g. of (II) ($R_1$=$C_2H_5$, X=F, $R_2$=H) in 30 ml. THF is added a sodium hydroxide solution (0.91 g) in 20 ml. water. The mixture is heated at 80° C. for 1 hour resulting in a clear solution which is evaporated under reduced pressure to dryness. The solid is dissolved in 200 ml. water and 2.5 ml. acetic acid is added. The resulting precipitate is filtered and washed with cold water, crystallized from dimethylformamide (DMF) to produce 1,2-difluoro-4-oxo-4H-quino[2,3,4-i,j][1,4]-benoxazine-5-carboxylic acid (II) ($R_1$=H, X=F, $R_2$=H).

(e) To a solution of 2.7 g. of 1,2-difluoro-4-oxo-4H-quino[2,3,4-i,j][1,4]benoxazine-5-carboxylic acid (II), ($R_1$=H, X=F, $R_2$=H) in 15 ml. of 1-methyl-2-pyrrolidinone at 115° C. is added 3 ml. piperazine. After stirring at 100° C. for 20 hours, the solvent is removed by reduced pressure to dryness. Ethanol is added to the residue and the resulting mixture is filtered and washed with ether and then washed with very small amounts of cold water to give (I) ($R_1$=H, $R_2$=H,

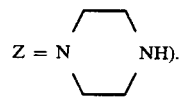

The resulting dried solid (I) is suspended in 30 ml. water and 8.5 ml. 1N HCl is added to and warmed to dissolve. Removal of the solvent under reduced pressure gives hydrochloride salt of 1-(1-piperazinyl)-2-fluoro-4-oxo-4H-quino[2,3,4-i,j][1,4]benoxazine-5-carboxylic acid (I) ($R_1$=H, $R_2$=H,

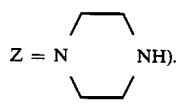

To the hydrochloride salt is added one molar equivalent of an aqueous solution of sodium hydroxide, and the resulting precipitate is filtered to obtain 1-(1- piperazinyl)-2-fluoro-4-oxo-4H-quino[2,3,4-i,j][1,4]benoxazine-5-carboxylic acid (I).

(f) Alternately, the title compound is prepared as follows: To a suspension of 5 g. of compound (II) (product of 1(d) in 40 ml. 1-methyl-2-pyrrolidinone at 120° C. under nitrogen atmosphere is added 9.5 ml. of N-carboethoxypiperazine. After 20 hours, the solvent is removed under reduced pressure and the residue is suspended in 150 ml. ethanol and refluxed for ½ hour. The reaction mixture is then cooled and filtered. The resulting solid is washed with cold ethanol and water to obtain compound (I). ($R_1$=H, $R_2$=H,

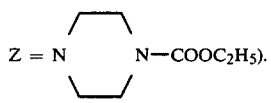

To a suspension of 5 g. of the preceding compound (I) ($R_1$=H, $R_2$=H,

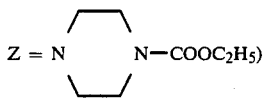

in 25 ml of ethanol at 80° C. is added 50 ml. of 10% NaOH solution. The solution is heated at 80° C. for 6 hours. The solvent is removed and the solid is dissolved in 100 ml water. The pH of the solution is adjusted to pH 7 by the addition of 10% acetic acid. The precipitate is filtered and washed with cold water yielding 1-(1-piperazinyl)-2-fluoro-4-oxo-4H-quino[2,3,4-i,j][1,4]-benoxazine-5-carboxylic acid (I) ($R_1$=H, $R_2$=H,

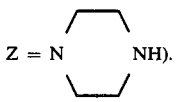

EXAMPLE 2

1-(1-(4-methyl)piperazinyl)-2-fluoro-4-oxo-4H-quino[2,3,4-i,j][1,4]benoxazine-5-carboxylic acid The procedure of Example 1 is repeated replacing piperazine in Example 1(e) with N-methylpiperazine to obtain 1-(1-(4-methyl)piperazinyl)-2-fluoro-4-oxo-4H-quino[2,3,4-i,j][1,4]benoxazine-5-carboxylic acid (I) ($R_1$=H, $R_2$=H,

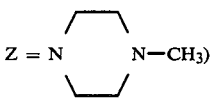

and its hydrochloride salt.

EXAMPLE 3

1-(1-pyrrolidinyl)-2-fluoro-4-oxo-4H-quino[2,3,4-i,j][1,4]benoxazine-5-carboxylic acid In the described fashion as Example 1, replacing piperazine in Example 1(e) with pyrrolidine, one can obtain 1-(1-pyrrolidinyl)-2-fluoro-4-oxo-4H-quino[2,3,4-i,j][1,4]benoxazine-5-carboxylic acid (I) ($R_1$=H, $R_2$=H,

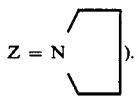

EXAMPLE 4

1-(1-3-hydroxypyrrolidinyl)-2-fluoro-4-oxo-4H-quino[2,3,4-i,j][1,4]benoxazine-5-carboxylic acid The procedure of Example 1 can be repeated replacing piperazine in Example 1(e) with 3-hydroxypyrrolidine to obtain 1-(1-3-hydroxypyrrolidinyl)-2-fluoro-4-oxo-4H-quino[2,3,4-i,j][1,4]benoxazine-5-carboxylic acid (I) ($R_1$=$R_2$=H,

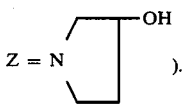

EXAMPLE 5

1-(1-3-aminopyrrolidinyl)-2-fluoro-4-oxo-4H-quino[2,3,4-i,j][1,4]benoxazine-5-carboxylic acid (a) In the described fashion as Example 1 replacing piperazine in Example 1(e) with 3-acetamidopyrrolidine, one can obtain 1-(1-3-acetamidopyrrolidinyl)-2-fluoro-4-oxo-4H-quino[2,3,4-i,j][1,4]benoxazine-5-carboxylic acid (I) ($R_1$=$R_2$=H,

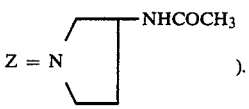

(b) The product of the above reaction can be hydrolyzed with hydrochloric acid at 80° C. to give 1-(1-3-aminopyrrolidinyl)-2-fluoro-4-oxo-4H-quino[2,3,4-i,j][1,4]benoxazine-5-carboxylic acid (I) ($R_1$=$R_2$=H,

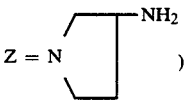

and its hydrochloride salt.

EXAMPLE 6

1-(1-3-methylaminopyrrolidinyl)-2-fluoro-4-oxo-4H-quino[2,3,4-i,j][1,4]benoxazine-5-carboxylic acid (a) In the described fashion as Example 1 replacing piperazine in Example 1(e) with 3-N-formyl-N-methyl-pyrrolidinyl, one can obtain 1-(1-3-N-formyl-N-methylaminopyrrolidinyl)-2-fluoro-4-oxo-4H-quino[2,3,4-i,j][1,4]benoxazine-5-carboxylic acid (I) ($R_1$=$R_2$=H,

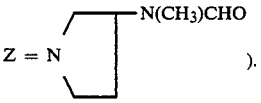

(b) The product of the above reaction can then be hydrolyzed with hydrochloric acid at 80° C. to give 1-(1-3-methylaminopyrrolidinyl)-2-fluoro-4-oxo-quino[2,3,4-i,j][1,4]benoxazine-5-carboxylic acid (I), ($R_1=R_2=H$,

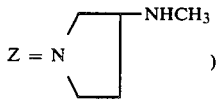
)

and its hydrochloride salt.

EXAMPLE 7

1-(1-3-dimethylaminopyrrolidinyl)-2-fluoro-4-oxo-4H-quino[2,3,4-i,j][1,4]benoxazine-5-carboxylic acid The procedure of Example 1 is repeated replacing piperazine in Example 1(e) with 3-dimethylaminopyrrolidine to obtain 1-(1-3-dimethylaminopyrrolidinyl)-2-fluoro-4-oxo-4H-quino[2,3,4-i,j][1,4]benoxazine-5-carboxylic acid (I) and its hydrochloride salt ($R_1=R_2=H$,

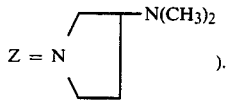
).

EXAMPLE 8

1-(1-piperidinyl)-2-fluoro-4-oxo-4H-quino[2,3,4-i,j][1,4]benoxazine-5-carboxylic acid The procedure of Example 1 can be repeated replacing piperazine in Example 1(e) with piperidine to obtain 1-(1-piperidinyl)-2-fluoro-4-oxo-4H-quino[2,3,4-i,j][1,4]benoxazine-5-carboxylic acid (I) ($R_1=R_2=H$,

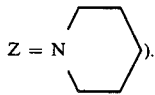
).

EXAMPLE 9

1-(4-morpholinyl)-2-fluoro-4-oxo-4H-quino[2,3,4-i,j][1,4]benoxazine-5-carboxylic acid In the described fashion as Example 1, replacing piperazine in Example 1(e) with morpholine, one can obtain 1-(4-morpholinyl)-2-fluoro-4-oxo-4H-quino[2,3,4-i,j][1,4]benoxazine-5-carboxylic acid (I) ($R_1=R_2=H$,

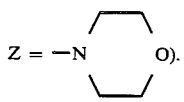
).

EXAMPLE 10

1-(4-thiomorpholinyl)-2-fluoro-4-oxo-4H-quino[2,3,4-i,j][1,4]benoxazine-5-carboxylic acid The procedure of Example 1 can be repeated replacing piperazine in Example 1(e) with thiomorpholine to obtain 1-(4-thiomorpholinyl)-2-fluoro-4-oxo-quino[2,3,4-i,j][1,4]benoxazine-5-carboxylic acid (I) ($R_1=R_2=H$,

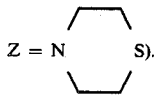
).

EXAMPLE 11

1-(1-3,5-dimethylpiperazinyl)-2-fluoro-4-oxo-4H-quino[2,3,4-i,j][1,4]benoxazine-5-carboxylic acid In the described fashion as Example 1, replacing piperazine in Examle 1(e) with 2,6-dimethylpiperazine, one obtains 1-(1-3,5-dimethylpiperazinyl)-2-fluoro-4-oxo-4H-quino[2,3,4-i,j][1,4]benoxazine-5-carboxylic acid (I) and its hydrochloride salt. ($R_1=R_2=H$,

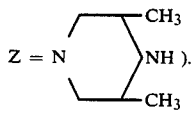
).

EXAMPLE 12

1-(1-homopiperazinyl)-2-fluoro-4-oxo-4H-quino[2,3,4-i,j][1,4]benoxazine-5-carboxylic acid The procedure of Example 1 is repeated replacing piperazine in Example 1(e) with homopiperazine to obtain 1-(1-homopiperazinyl)-2-fluoro-4-oxo-4H-quino[2,3,4-i,j][1,4]benoxazine-5-carboxylic acid (I) and its hydrochloride salt ($R_1=R_2=H$,

).

EXAMPLE 13

1-dimethylamino-2-fluoro-4-oxo-4H-quino[2,3,4-i,j][1,4]benoxazine-5-carboxylic acid In the described fashion as Example 1, replacing piperazine in Example 1(e) with dimethylamine, one can obtain 1-dimethylamino-2-fluoro-4-oxo-4H-quino[2,3,4-i,j][1,4]benoxazine-5-carboxylic acid (I) ($R_1=R_2=H$, $Z=N(CH_3)_2$).

EXAMPLE 14

1-(N-2-hydroxyethylamino)-2-fluoro-4-oxo-4H-quino[2,3,4-i,j][1,4]benoxazine-5-carboxylic acid The procedure of Example 1 can be repeated replacing piperazine in Example 1(e) with N-2-hydroxyethylamine to obtain 1-(N-2-hydroxyethylamino)-2-fluoro-4-oxo-4H-quino[2,3,4-i,j][1,4]benoxazine-5-carboxylic acid (I) ($R_1=R_2=H$, $X=NHC_2H_4-OH$).

EXAMPLE 15

1-hydrazyl-2-fluoro-4-oxo-4H-quino[2,3,4-i,j][1,4]benoxazine-5-carboxylic acid

In the described fashion as Example 1, replacing piperazine in Example 1(e) with hydrazine, one can obtain 1-hydrazyl-2-fluoro-4-oxo-4H-quino[2,3,4- i,j][1,4]benozazine-5-carboxylic acid ($R_1=R_2=H$, $Z=NHNH_2$).

EXAMPLE 16

1-(1-piperazinyl)-2,10-difluoro-4-oxo-4H-quino[2,3,4-i,j][1,4]benoxazine-5-carboxylic acid (a) In the described fashion as Example 1(b), replacing 2-hydroxyaniline with 2-hydroxy-4-fluoroaniline, one can obtain the enaminoketoester (6) ($R_1=C_2H_5$, R=10-fluoro, X=F).

(b) By following the Example 1(c) and 1(d), the preceding compound (6) can yield 1,2,10-trifluoro-4-oxo-4H-quino[2,3,4-i,j][1,4]benoxazine-5-carboxylic acid (II), ($R_1=H$, X=F, $R_2=10$-fluoro.

(c) In the described fashion as Example 1(e), the above acid (II) can give the desired 1-(1-piperazinyl)-2,10-difluoro-4-oxo-4H-quino[2,3,4-i,j][1,4]benoxazine-5-carboxylic acid (I) and its hydrochloride salt ($R_1=H$, $R_2=10$-fluoro,

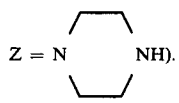

EXAMPLE 17

In the described fashion as Example 1(e), replacing the acid (II) ($R_1=R_2=H$, X=F) with the acid (II) of the product of Example 16(b) ($R_1=H$, $R_2=10$-fluoro, X=F) and also replacing piperazine with an appropriate amine such as N-methylpiperazine, pyrrolidine, 3-hydroxypyrrolidine, 3-acetaminopyrrolidine, 3-N-formyl-N-methylaminopyrrolidine, 3-dimethylaminopyrrolidine, piperidine, morpholine, thiomorpholine, 2,6-dimethylpiperazine, homopiperazine, diethylamine and 2,2-dimethylhydrazine, one can obtain the following compounds:

(a) 1-(1-4-methylpiperazinyl)-2,10-difluoro-4-oxo-4H-quino[2,3,4-i,j][1,4]benoxazine-5-carboxylic acid (I) and its hydrochloride salt ($R_1=H$, $R_2=10$-fluoro,

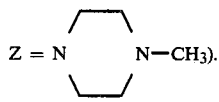

(b) 1-(1-pyrrolidinyl)-2,10-difluoro-4-oxo-4H-quino[2,3,4-i,j][1,4]benoxazine-5-carboxylic acid (I) ($R_1=H$, $R_2=10$-fluoro,

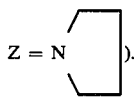

(c) 1-(1-3-hydroxypyrrolidinyl)-2,10-difluoro-4-oxo-4H-quino[2,3,4-i,j][1,4]benoxazine-5-carboxylic acid (I) ($R_1H$, $R_2=10$-fluoro,

(d) 1-(1-3-acetamidopyrrolidinyl)-2,10-difluoro-4-oxo-4H-quino[2,3,4-i,j][1,4]benoxazine-5-carboxylic acid (I) ($R_1=H$, $R_2=10$-fluoro,

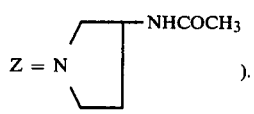

(e) 1-(1-3-N-formyl-N-methylaminopyrrolidinyl)-2,10-difluoro-4-oxo-4H-quino[2,3,4-i,j][1,4]benoxazine-5-carboxylic acid (I) ($R_1=H$, $R_2=10$-fluoro,

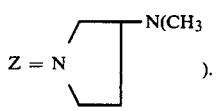

(f) 1-(1-3-dimethylaminopyrrolidinyl)-2,10-difluoro-4-oxo-4H-quino-[2,3,4-i,j][1,4]benoxazine-5-carboxylic acid (I) ($R_1=H$, $R_2=10$-fluoro,

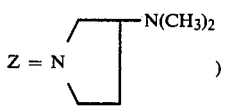

and its hydrochloride salt.

(g) 1-(1-piperidinyl)-2,10-difluoro-4-oxo-4H-quino[2,3,4-i,j][1,4]benoxazine-5-carboxylic acid (I) ($R_1H$, $R_2=10$-fluoro,

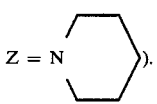

(h) 1-(4-morpholinyl)-2,10-difluoro-4-oxo-4H-quino[2,3,4-i,j][1,4]benoxazine-5-carboxylic acid (I) ($R_1=H$, $R_2=10$-fluoro,

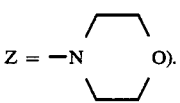

(i) 1-(4-thiomorpholinyl)-2,10-difluoro-4-oxo-4H-quino[2,3,4-i,j][1,4]benoxazine-5-carboxylic acid (I) ($R_1=H$, $R_2=10$-fluoro,

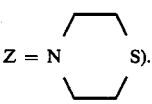

(j) 1-(1-3,5-dimethylpiperazinyl)-2,10-difluoro-4-oxo-4H-quino-[2,3,4-i,j][1,4]benoxazine-5-carboxylic acid (I) ($R_1=H$, $R_2=10$-fluoro,

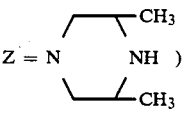

and its hydrochloride salt.

(k) 1-(1-homopiperazinyl)-2,10-difluoro-4-oxo-4H-quino[2,3,4-i,j][1,4]benoxazine-5-carboxylic acid (I) (R₁H, R₂=10-fluoro,

and its hydrochloride salt.

(l) 1-diethylamino-2,10-difluoro-4-oxo-4H-quino[2,3,4-i,j][1,4]benoxazine-5-carboxylic acid (I) (R₁=H, R₂=10-fluoro, Z=N(CH₃)₂).

(m) 1N,N-dimethylhydrazyl-2,10-difluoro-4-oxo-4H-quino[2,3,4-i,j][1,4]benoxazine-5-carboxylic acid (I) (R₁=H, R₂=10-fluoro, Z=NHN(CH₃)₂).

EXAMPLE 18

In the described fashion of Example 5(b), the compounds of Examples 17(d) and 17(e) can give the following 2 compounds.

(a) 1-(1-3-aminopyrrolidinyl)-2,10-difluoro-4-oxo-quino[2,3,4-i,j][1,4]benoxazine-5-carboxylic acid (I) and its hydrochloride salt (R₁=H, R₂=1-fluoro,

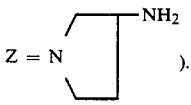

(b) 1-(1-3-methylaminopyrrolidinyl)-2,10-difluoro-4-oxo-4H-quino[2,3,4-i,j][1,4]benoxazine-5-carboxylic acid (I) and its hydrochloride salt (R₁=H, R₂=10-fluoro,

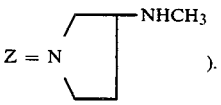

EXAMPLE 19

In the described fashion as Example 1(a–d), replacing o-hydroxyaniline with an appropriate substituted

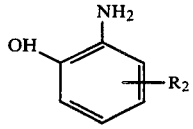

one can obtain the additional substituted 1,2-difluoro-4-oxo-4H-quino[2,3,4-i,j][1,4]benoxazine-5-carboxylic acid (II) as listed in Table I.

TABLE I

| Substituted 2-hydroxyaniline | Compound (II) (R₁ = H, X = F) obtained |
|---|---|
| 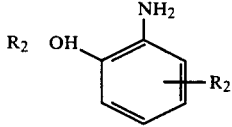 | R₂ |
| (a) 4-methoxy | 10-methoxy |
| (b) 4-methyl | 10-methyl |
| (c) 4-chloro | 10-chloro |
| (d) 4,6-difluoro | 8,10-difluoro |
| (e) 4,6-methylenedioxy | 9,10-methylenedioxy |
| (f) 4-hydroxy | 10-hydroxy |
| (g) 4-dimethylamino | 10-dimethylamino |
| (h) 5-fluoro | 9-fluoro |

EXAMPLE 20

In the described fashion of Example 1(e), replacing the acid (II) (R₁=H, R₂=H, X=F) with the acid (II) of the compounds listed in Table I of Example 19 and also replacing piperazine with an appropriate amine such as N-methylpiperazine, pyrrolidine, 3-hydroxypyrrolidine, 3-acetamidopyrrolidine, 3-N-formyl-N-methylaminopyrrolidine, 3-dimethylaminopyrrolidine, piperidine, morpholine, thiomorpholine, 2,6-dimethylpiperazine, homopiperazine, dimethylamine and 2,2-dimethylhydrazine, and extra hydrolysis step if required as in Example 5(b), one can obtain the following additional compounds (I) as summarized in Table II.

TABLE II

| Piperazine replacement ZH | Compound II used (R₁ = H, X = F) R₂ | Compound I obtained (R₁ = H) R₂ | Z |
|---|---|---|---|
| 1. piperazine | 8,10-difluoro | 8,10-difluoro | piperazinyl |
| 2. piperazine | 9,10-methylenedioxy | 9,10-methylenedioxy | piperazinyl |
| 3. piperazine | 10-hydroxy | 10-hydroxy | piperazinyl |
| 4. piperazine | 10-methyl | 10-methyl | piperazinyl |
| 5. 4-methylpiperazine | 8,10-difluoro | 8,10-difluoro | 4-methylpiperazinyl |
| 6. 4-methylpiperazine | 9,10-methylenedioxy | 9,10-methylenedioxy | 4-methylpiperazinyl |
| 7. 4-methylpiperazine | 10-hydroxy | 10-hydroxy | 4-methylpiperazinyl |
| 8. 4-methylpiperazine | 10-chloro | 10-chloro | 4-methylpiperazinyl |
| 9. 3-acetamidopyrrolidine | 8,10-difluoro | 8,10-difluoro | 3-aminopyrrolidinyl |
| 10. 3-acetamidopyrrolidine | 9,10-methylenedioxy | 9,10-methylenedioxy | 3-aminopyrrolidinyl |
| 11. 3-acetamidopyrrolidine | 10-hydroxy | 10-hydroxy | 3-aminopyrrolidinyl |
| 12. 3-acetamidopyrrolidine | 9-fluoro | 9-fluoro | 3-aminopyrrolidinyl |
| 13. 3-methylacetamidopyrrolidine | 8,10-difluoro | 8,10-difluoro | 3-methylaminopyrrolidinyl |
| 14. 3-methylacetamidopyrrolidine | 9,10-methylenedioxy | 9,10-methylenedioxy | 3-methylaminopyrrolidinyl |
| 15. 3-methylacetamidopyrrolidine | 10-hydroxy | 10-hydroxy | 3-methylaminopyrrolidinyl |
| 16. 3-methylacetamidopyrrolidine | 10-dimethylamino | 10-dimethylamino | 3-methylaminopyrrolidinyl |
| 17. pyrrolidine | 10-methoxy | 10-methoxy | pyrrolidinyl |
| 18. 3-dimethylamino- | 9,10-methylenedioxy | 9,10-methylenedioxy | 3-dimethylaminopyrrolidinyl |

TABLE II-continued

| Piperazine replacement ZH | Compound II used (R₁ = H, X = F) R₂ | Compound I obtained (R₁ = H) R₂ | Z |
|---|---|---|---|
| pyrrolidine | | | |
| 19. 3-dimethylamino-pyrrolidine | 8,10-difluoro | 8,10-difluoro | 3-dimethylaminopyrrolidinyl |
| 20. 3-hydroxypyrrolidine | 9-fluoro | 9-fluoro | 3-hydroxypyrrolidinyl |
| 21. piperidine | 10-hydroxy | 10-hydroxy | piperidinyl |
| 22. morpholine | 10-chloro | 10-chloro | morpholinyl |
| 23. thiomorpholine | 10-methyl | 10-methyl | thiomorpholinyl |
| 24. N,N—dimethylhydrazine | 10-methoxy | 10-methoxy | N,N—dimethylhydrazyl |
| 25. dimethylamine | 10-chloro | 10-chloro | dimethylamino |
| 26. homopiperazine | 8,10-difluoro | 8,10-difluoro | homopiperazinyl |
| 27. 2,6-dimethylpiperazine | 9,10-methylenedioxy | 9,10-methylenedioxy | 3,5-dimethylpiperazinyl |

It will be understood that various changes and modifications can be made in the details of procedure, formulation and use without departing from the spirit of the invention, especially as defined in the following claims.

What is claimed is:

1. A compound having the formula:

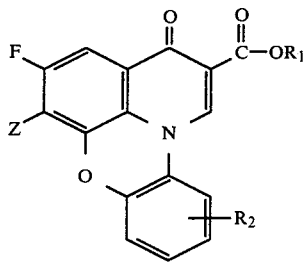

wherein $R_1$ is hydrogen or a carboxy protecting group; $R_2$ is one or more groups selected from the group consisting of hydrogen, halogen, nitro, carboxyl, methylenedioxy, cyano, $C_1$ to $C_6$ alkyl, halo-substituted $C_1$ to $C_6$ alkyl, hydroxy-substituted $C_1$ to $C_6$ alkyl, a group having the formula:

wherein —Y— is —O— or —S— and $R_3$ is hydrogen or $C_1$ to $C_6$ alkyl, and an amine group having the formula:

wherein $R_4$ and $R_5$ are independently hydrogen or $C_1$ to $C_6$ alkyl; and Z is selected from the group consisting of a saturated heterocyclic ring having the structure:

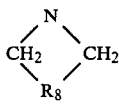

wherein $R_8$ is dimethylene, —CH₂—CH₂—CH₂—, CH₂—CH₂—NH—CH₂—, or a group of the formula —CH₂—R₉—CH₂— wherein $R_9$ is selected from the group consisting of —S—, —O— and —NH—; substituted derivatives thereof having one or more substituents selected from the group consisting of $C_1$ to $C_6$ alkyl, $C_1$ to $C_6$ hydroxyalkyl, hydroxy, alkanoyl containing 1 to 6 carbon atoms, alkanoylamido containing 1 to 6 carbon atoms and an amine of the formula:

wherein $R_{10}$ and $R_{11}$ are each independently selected from the group consisting of hydrogen and $C_1$ to $C_6$ alkyl; and an amino group of the formula:

wherein $R_6$ is hydrogen or $C_1$ to $C_{10}$ alkyl; and $R_7$ is selected from the group consisting of $C_1$ to $C_{10}$ alkyl, hydroxy-substituted $C_1$ to $C_{10}$ alkyl, an amino group, a mono-($C_1$ to $C_6$) alkylamino group and a di-($C_1$ to $C_6$) alkylamino group, and pharmaceutically acceptable salts thereof.

2. A compound as defined in claim 1 wherein the saturated heterocyclic ring is selected from the group consisting of azetidinyl groups, piperazinyl groups, 4-acylpiperazinyl groups, piperidinyl groups, pyrrolidinyl groups, morpholino groups, thiomorpholino groups and homopiperazinyl groups.

3. A compound as defined in claim 1 wherein $R_1$ is hydrogen.

4. A compound as defined in claim 1 wherein Z is an amino group having the formula:

wherein $R_6$ is hydrogen, or $C_1$ to $C_{10}$ alkyl and $R_7$ is $C_1$ to $C_{10}$ alkyl, or hydroxy-substituted $C_1$ to $C_{10}$ alkyl, an amino group, a mono-($C_1$-$C_4$) alkylamino group or a di($C_1$-$C_4$) alkylamino group.

5. A compound having the formula:

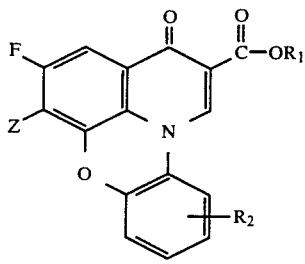

wherein Z is piperazinyl or piperazinyl substituted with a $C_1$ to $C_6$ alkyl, or 4-acylpiperazinyl, or 3-amino-pyrrolidinyl or 3-$C_1$ to $C_6$ alkylamino-pyrrolidinyl; and $R_2$ is one or more of hydrogen, an alkyl group, a halogen group, a hydroxy group, and a methylenedioxy group, and pharmaceutically acceptable salts thereof.

6. A compound as defined in claim 5 wherein $R_2$ is hydrogen; Z is piperazinyl; and $R_1$ is hydrogen.

7. A compound as defined in claim 5 wherein $R_2$ is hydrogen; Z is 4-methylpiperazinyl; and $R_1$ is hydrogen.

8. A compound as defined in claim 5 wherein $R_2$ is 10-fluoro; Z is piperazinyl and $R_1$ is hydrogen.

9. A compound as defined in claim 5 wherein $R_2$ is 10-fluoro, Z is 4-methylpiperazinyl and $R_1$ is hydrogen.

10. A compound as defined in claim 5 wherein $R_2$ is 10-fluoro, Z is 3-aminopyrrolidinyl and $R_1$ is hydrogen.

11. A compound as defined in claim 5 wherein $R_2$ is 10-fluoro, Z is 3-methylaminopyrrolidinyl and $R_1$ is hydrogen.

12. A compound as defined in claim 5 wherein $R_2$ is 10-fluoro, Z is dimethylaminopyrrolidinyl and $R_1$ is hydrogen.

13. A compound as defined in claim 5 wherein $R_2$ is 8,10-difluoro, Z is 4-methylpiperazinyl and $R_1$ is hydrogen.

14. A composition having antibacterial activity in pharmaceutical dosage form containing a diluent and a compound as defined in claim 1.

15. A composition having antibacterial activity in pharmaceutical dosage form containing a diluent and a compound as defined in claim 5.

16. A method of treating a bacterial infection in a patient comprising administering to a patient in need of such treatment a therapeutically effective amount of a compound as defined in claim 1.

17. A method of treating a bacterial infection in a patient comprising administering to a patient in need of such treatment a therapeutically effective amount of a compound as defined in claim 5.

* * * * *